(12) United States Patent
Fantuzzi et al.

(10) Patent No.: US 9,808,550 B2
(45) Date of Patent: Nov. 7, 2017

(54) SCENT DELIVERY SYSTEM

(71) Applicant: Pacific Precision Products Mfg., Irvine, CA (US)

(72) Inventors: Emmanuel Fantuzzi, Champs sur Marne (FR); Ricardo Padilla, Jr., Orange, CA (US); Loong Sang Yong, Irvine, CA (US); Ritu Raj Kamal, Ladera Ranch, CA (US); Dillon Connolly, Costa Mesa, CA (US); Romain Ducos, Huntington Beach, CA (US)

(73) Assignee: PACIFIC PRECISION PRODUCTS MFG., Irvine, CA (US)

( * ) Notice: Subject to any disclaimer, the term of this patent is extended or adjusted under 35 U.S.C. 154(b) by 77 days.

(21) Appl. No.: 14/942,734

(22) Filed: Nov. 16, 2015

(65) Prior Publication Data
US 2016/0263265 A1  Sep. 15, 2016

Related U.S. Application Data

(60) Provisional application No. 62/132,433, filed on Mar. 12, 2015, provisional application No. 62/132,431, filed on Mar. 12, 2015.

(51) Int. Cl.
*A61L 9/12* (2006.01)
*B01F 3/04* (2006.01)

(52) U.S. Cl.
CPC .......... *A61L 9/122* (2013.01); *B01F 3/04085* (2013.01); *A61L 2209/133* (2013.01)

(58) Field of Classification Search
CPC ......... A61L 9/122; B01F 3/04; B01F 3/04085

USPC ....................... 261/26, 30, DIG. 88; 422/124
See application file for complete search history.

(56) References Cited

U.S. PATENT DOCUMENTS

| | | | |
|---|---|---|---|
| 2,608,436 A | * | 8/1952 | Baughman .............. A61L 9/122 239/47 |
| 4,111,655 A | | 9/1978 | Quincey |
| 4,345,700 A | | 8/1982 | Souza |
| 5,011,632 A | | 4/1991 | Yano et al. |
| 5,610,674 A | | 3/1997 | Martin |
| 5,898,475 A | | 4/1999 | Martin |

(Continued)

FOREIGN PATENT DOCUMENTS

GB    2233230    9/1991

OTHER PUBLICATIONS

International Search Report and Written Opinion issued in PCT/US2016/021579 dated May 17, 2016.

*Primary Examiner* — Robert A Hopkins
(74) *Attorney, Agent, or Firm* — Jeffer Mangels; Butler & Mitchell LLP; Brennan C. Swain, Esq.

(57) ABSTRACT

A scent delivery assembly that includes a main body portion that defines an interior and includes at least one intake opening and at least one outlet opening, an airflow path that is defined between the intake opening and the outlet opening, a fan positioned along the airflow path, and at least a first cartridge positioned along the airflow path. The first cartridge includes a first cover that is movable between a closed position and an open position and a scent assembly. The scent assembly is not in flow communication with the airflow path when the first cover is in the closed position, and the scent assembly is in flow communication with the airflow path when the first cover is in the open position.

18 Claims, 13 Drawing Sheets

(56) References Cited

U.S. PATENT DOCUMENTS

| | | |
|---|---|---|
| 6,319,117 B1 | 11/2001 | Moore |
| 6,783,117 B2 * | 8/2004 | Wohrle .................. A61L 9/035 261/104 |
| 7,185,260 B2 | 2/2007 | Anton |
| 7,651,077 B1 | 1/2010 | Rosener et al. |
| 8,602,396 B1 | 12/2013 | V et al. |
| 2006/0074742 A1 | 4/2006 | Santandrea |
| 2006/0251541 A1 | 11/2006 | Santandrea |
| 2010/0197189 A1 | 8/2010 | Jin |
| 2010/0284783 A1 | 11/2010 | Lolmede |
| 2011/0089252 A1 | 4/2011 | Rosener et al. |
| 2012/0018530 A1 | 1/2012 | Blaylock et al. |
| 2014/0183762 A1 | 7/2014 | Suissa et al. |
| 2015/0019030 A1 | 1/2015 | Chandler et al. |

* cited by examiner

SCENT DELIVERY SYSTEM

CROSS REFERENCE TO RELATED APPLICATIONS

This application claims the benefit of U.S. Provisional Application No. 62/132,431, filed Mar. 12, 2015 and U.S. Provisional Application No. 62/132,433, filed Mar. 12, 2015, both of which are incorporated by reference herein in their entireties.

FIELD OF THE INVENTION

The present invention relates generally to a scent delivery system, and more particularly for a scent delivery system for use in an aircraft.

BACKGROUND OF THE INVENTION

Aircraft often include confined spaces. A passenger's experience within those confined spaces can be improved through better scents. High end scent generation is today available in multiple forms. For example, scent marketing is used to enhance customer experience in retail stores, food and beverage stores, casino and hotels. The aim is typically to put the customer in a positive mood to trigger buying action or to provide signature fragrance (hotel chains). Airline lounges also use scent generation to improve the customer experience.

SUMMARY OF THE PREFERRED EMBODIMENTS

In accordance with a first aspect of the present invention there is provided a scent delivery assembly that includes a main body portion that defines an interior and includes at least one intake opening and at least one outlet opening, an airflow path that is defined between the intake opening and the outlet opening, a fan positioned along the airflow path, and at least a first cartridge positioned along the airflow path. The first cartridge includes a first cover that is movable between a closed position and an open position and a scent assembly. The scent assembly is not in flow communication with the airflow path when the first cover is in the closed position, and the scent assembly is in flow communication with the airflow path when the first cover is in the open position. In a preferred embodiment, the scent assembly includes a reservoir portion and a diffusing portion. Preferably, the scent delivery system also includes a second and third cartridges positioned along the airflow path. In a preferred embodiment, each of the cartridges has a different scent associated therewith. Preferably, the scents are chosen to affect a user or passenger's mood. For example, the scents can be chosen to energize, calm, relax, etc. Preferably, the scent delivery assembly also includes a controller that is configured to selectively move the first, second and third covers between the open and closed positions.

In a preferred embodiment the scent delivery assembly includes a first actuator that includes a first arm that is movable between a first position and a second position. The first cartridge is attached to a distal end of the first arm. When the first arm is in the first position the first cover is in the closed position and when the first arm is in the second position the first cover is in the open position. Preferably, the main body portion includes a divider member positioned in the interior that divides the interior into an airflow path portion and a non-airflow path portion. The first cartridge is position in the airflow path portion and the first actuator is position in the non-airflow path portion.

In a preferred embodiment, the first cartridge includes a housing portion and the cover portion. The housing portion includes an attachment opening therein and the distal end of the first actuator arm is releasably received in the attachment opening. Preferably, when the first cover is in the closed position the scent assembly is not aligned with the airflow path and when the first cover is in the open position the scent assembly is generally aligned with the airflow path. In a preferred embodiment, the scent delivery system includes at least first and second positioning pegs positioned adjacent an exterior surface of the first cartridge.

In a preferred embodiment, the scent delivery system includes a motor that is operable to move the first cover between the open and closed positions. In a preferred embodiment, the first cartridge includes a second cover that is movable via the motor together with the first cover between the closed position and the open position and the scent assembly is positioned in the airflow path between the first cover and the second cover. In a preferred embodiment, the main body portion includes a lower housing portion and an upper housing portion that cooperate to define the interior and the intake opening is defined in the lower housing portion and the outlet opening is defined in the upper housing portion. Preferably, the scent delivery system includes a removable tray portion received in a tray portion recess defined in the lower housing portion. The tray portion includes a first cartridge opening defined therethrough and the first cartridge is removably received in the first cartridge opening. Preferably, the upper housing portion is pivotally connected to the lower housing portion. In a preferred embodiment, the motor includes an arm extending therefrom that is configured to move the first cover between the open and closed positions. Preferably, the cartridge is sealed when it is in the closed position.

In a preferred embodiment, the first, second and third cartridges each include a scent associated therewith and are configured to communicate the scent to the controller. Preferably, the controller is configured to communicate the scent identification to a control panel (e.g., a tablet, smart phone, etc.) that includes a user interface (such as a graphical user interface on the tablet).

The present invention provides the ability to enrich the air within the cabin of an aircraft with a predetermined scent. In other words, the present invention provides the ability to deliver a scent from a fragrance or the like to a passenger onboard an aircraft.

In a preferred embodiment, the invention includes scent cartridges and a control panel (such as a tablet or other remote control) for controlling the delivery of the scented air.

When used, the present invention can enhancing passengers' mood on an aircraft. In a preferred embodiment, the system includes the ability to control at least one of the scent of the cabin, the lighting (mood lighting), the music, the inflight entertainment and the cabin temperature. The ability to control one or all of these items helps set the mood of the cabin and can bring added value to the passenger experience. Being able to control remotely or not the scent/fragrance diffused in the cabin or part of the cabin (e.g., a private room) of an aircraft together with ambient/personal lights and/or sound (music) and/or entertainment system and/or environmental control system provide the ability to diffuse and control the scent in the cabin/part of cabin. Combined control of ambiance featured by the different scent diffused in the cabin and/or the light and/or sound effect to set a specific mood.

The control panel/tablet can be in communication with the controller within the scent delivery system via a wired or wireless (e.g., Wi-Fi) connection. Preferably, the scent delivery system includes a plurality of cartridges that can provide different scents as desired by the user. The controller also preferably controls the fan settings (e.g., speed, duration, number of cycles, etc.). For example, the fan may run one minute on and then two minutes off or two minutes at a reduced speed. The controller also preferably controls the opening and closing of the cartridges to enhance the scent experience by passengers.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENTS

Figure 1:
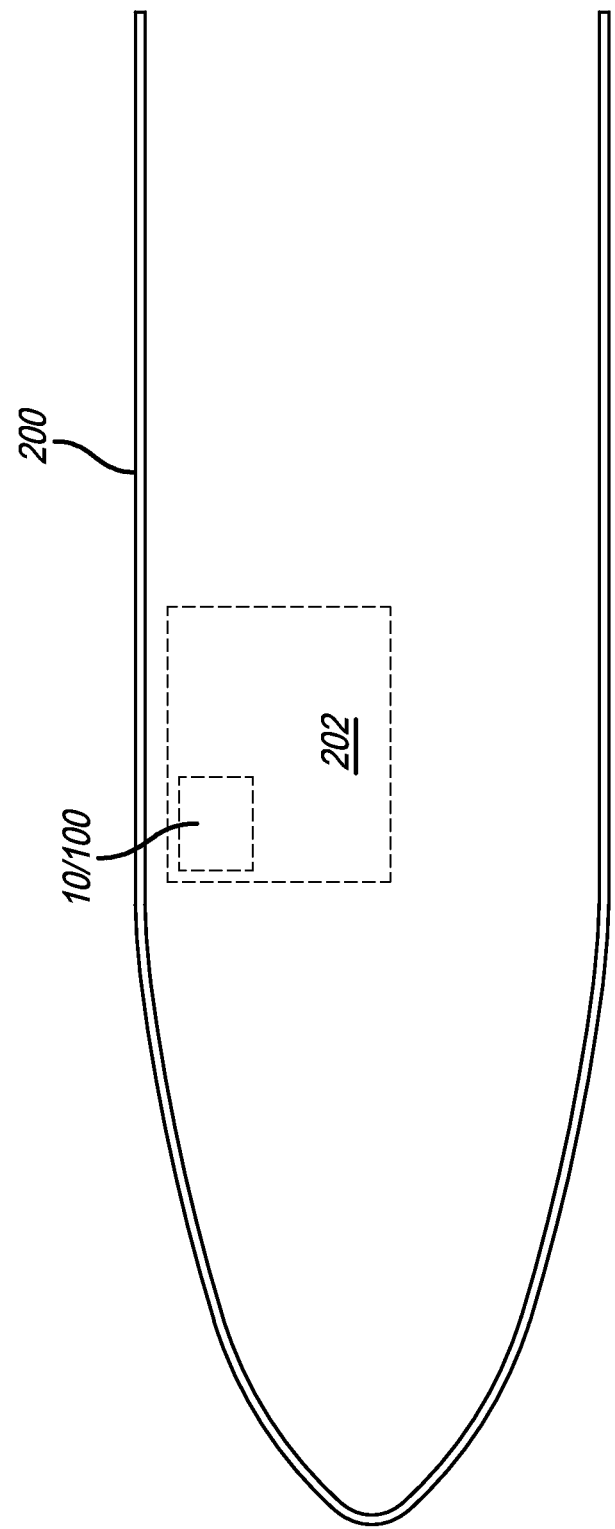
FIG. 1 is a plan view of an aircraft with a private room therein that includes a scent delivery system in accordance with a preferred embodiment of the present invention.
Figure 2:
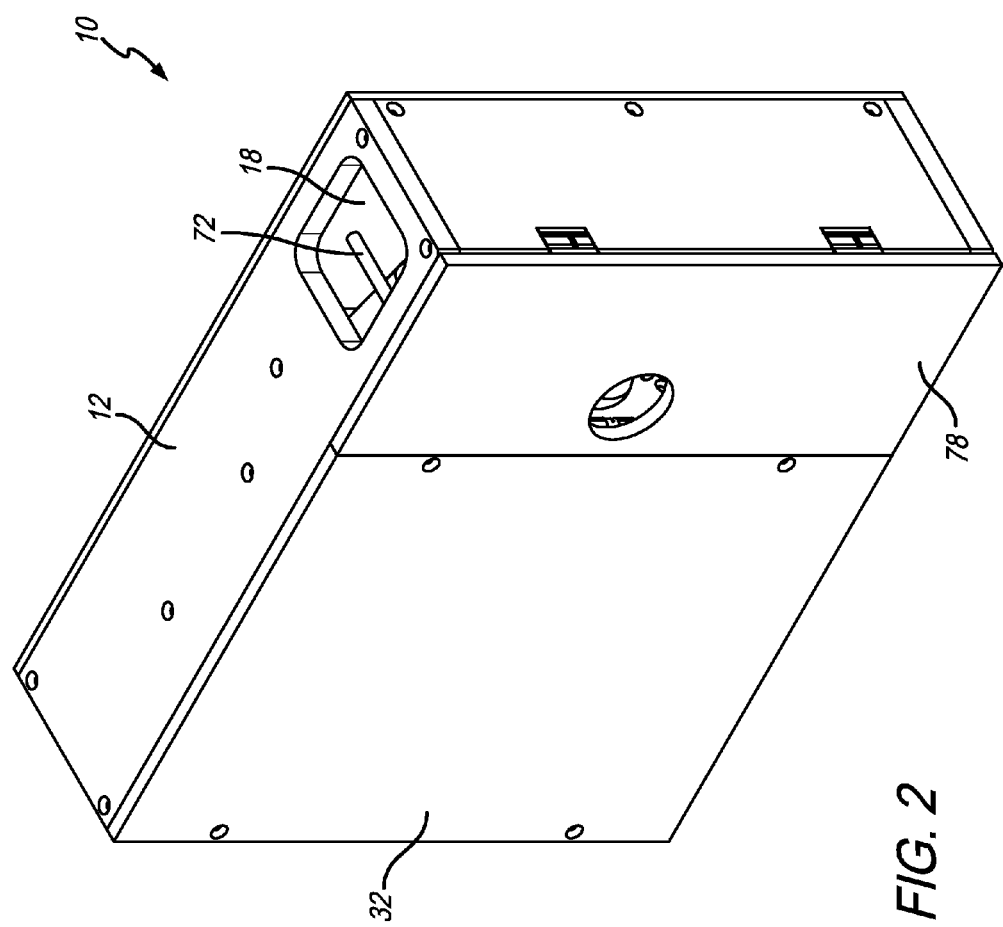
FIG. 2 is a perspective view of a scent delivery assembly in accordance with a preferred embodiment of the present invention.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments.

Reference in this specification to "one embodiment" or "an embodiment" means that a particular feature, structure, or characteristic described in connection with the embodiment is included in at least one embodiment of the-disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present invention.

Referring now to the drawings, wherein the showings are for purposes of illustrating the present invention and not for purposes of limiting the same, FIGS. 1-13 show embodiments of scent delivery systems or assemblies 10 and 100. In a preferred embodiment, the scent delivery assemblies are used in the interior of aircraft, as shown in FIG. 1. However, this is not a limitation on the present invention and the scent delivery assemblies 10 and 100 can be used elsewhere. 10.

Figure 3:
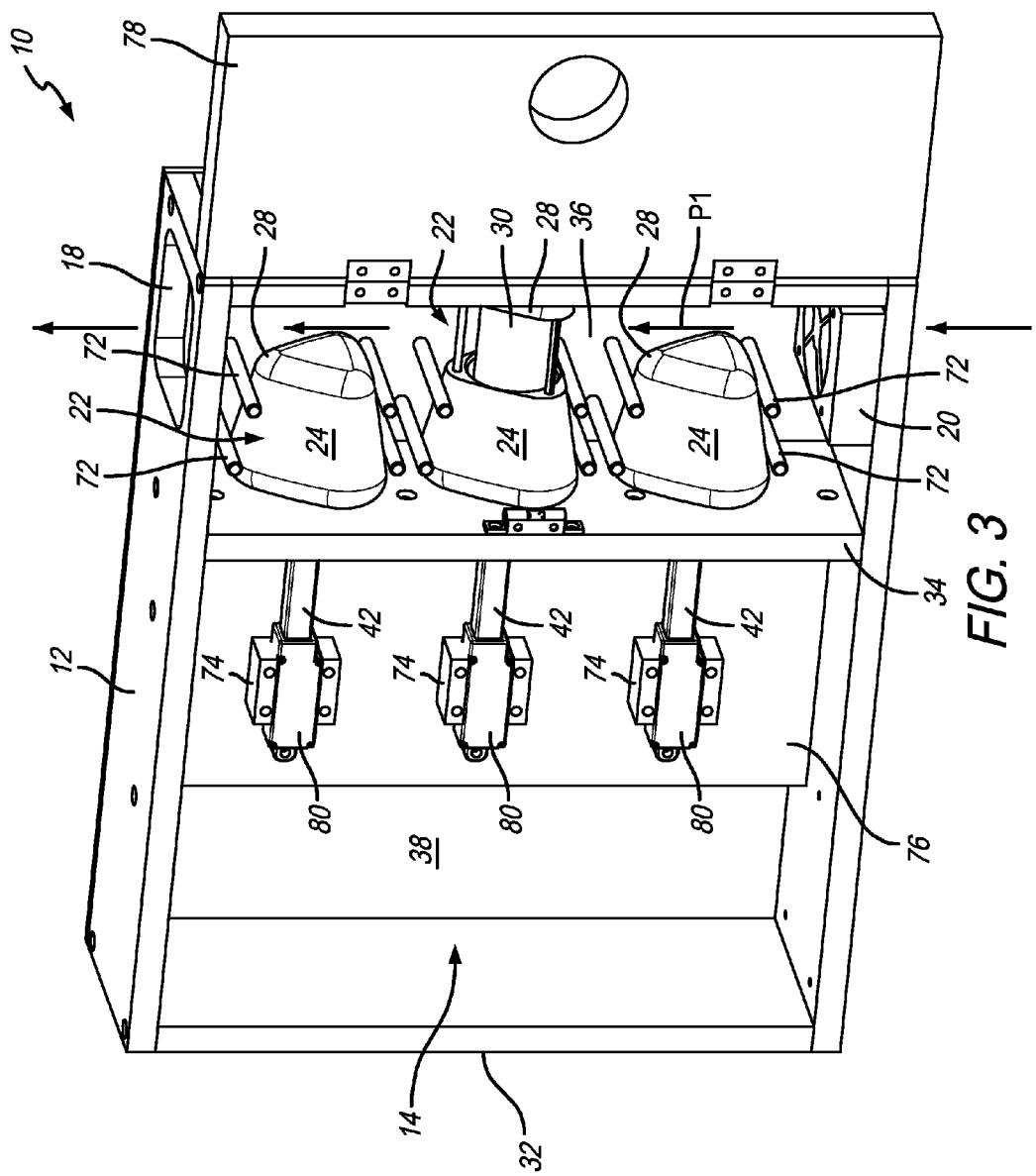
FIG. 3 is a perspective view of the scent delivery assembly of FIG. 1 with a portion of the housing removed.
Figure 4:
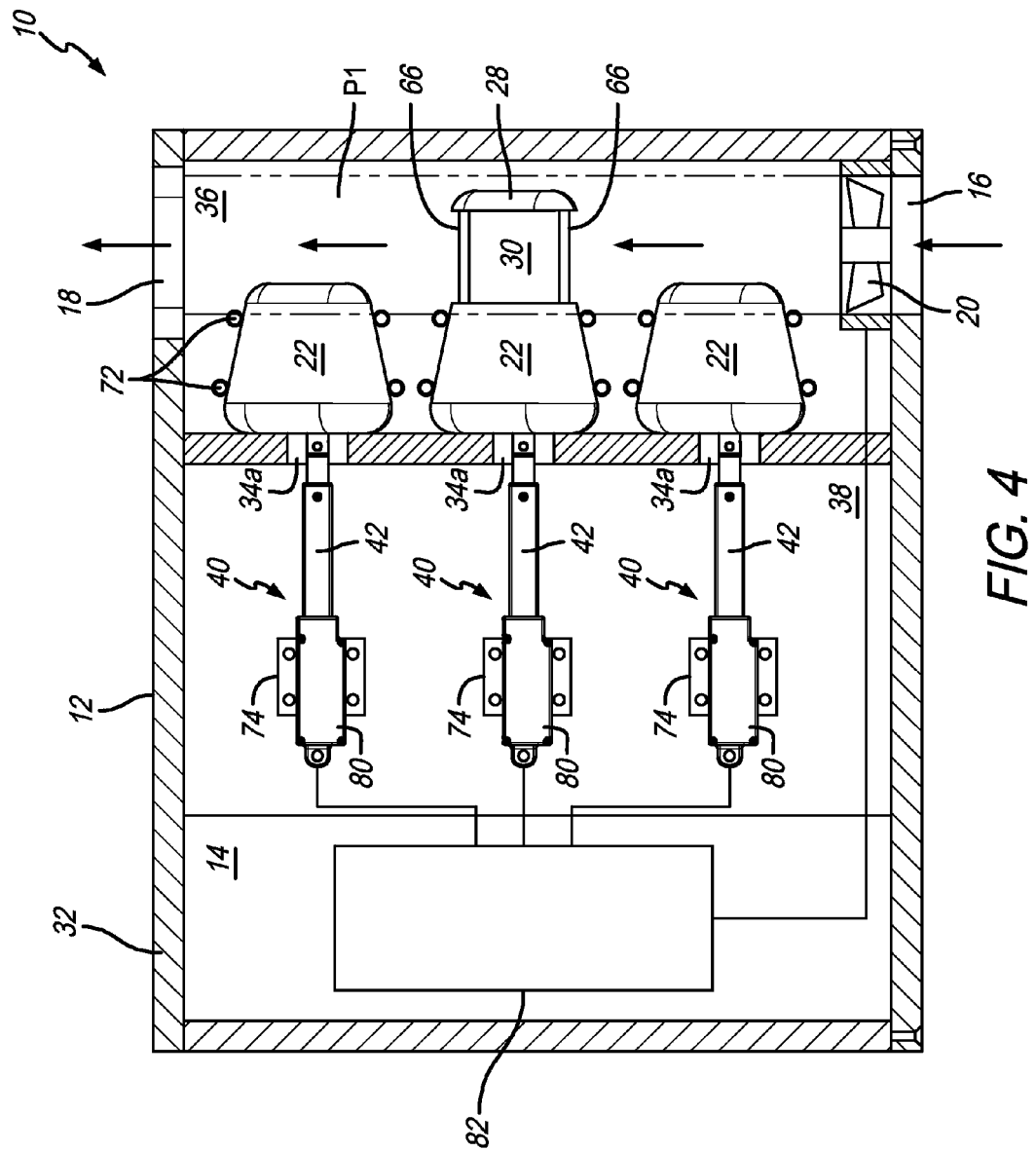
FIG. 4 is a cross-sectional elevational view of the scent delivery assembly of FIG. 1.

With reference to FIGS. 2-8, scent delivery assembly 10 is shown and described. In a preferred embodiment, scent delivery assembly 10 includes a main body portion 12 that defines an interior 14 and includes at least one intake opening 16 and at least one outlet opening 18. As shown in FIGS. 3-4, an airflow path P1 is defined between the intake opening 16 and the outlet opening 18. A fan 20 is positioned along the airflow path P1. At least one and preferably a plurality of cartridges 22 are positioned along the airflow path P1. Each cartridge 22 includes a housing portion 24 that defines a housing interior 26, a cover 28 and a scent assembly 30 positioned in the housing interior 26. The cover 28 is movable between a closed position and an open position. In a preferred embodiment, the scent assembly 30 is movable together with the cover 28 between the closed and opened positions. The scent assembly 30 is not in flow communication with the airflow path P1 when the cover 28 is in the closed position and is in flow communication with the airflow path P1 when the cover 28 is in the open position. FIGS. 3-4 show the middle cartridge 22 with the cover 28 and scent assembly 30 in the open position and the top and bottom cartridges 22 with the cover 28 and scent assembly 30 in the closed position.

As shown in FIGS. 2-5, the main body portion 12 includes a housing 32 having a divider member 34 that divides the interior 14 into an airflow path portion 36 and a non-airflow path portion 38. The cartridges 22 are positioned in the in the airflow path portion 36 and a plurality of actuators 40 are positioned in the non-airflow path portion 38.

Figure 6:
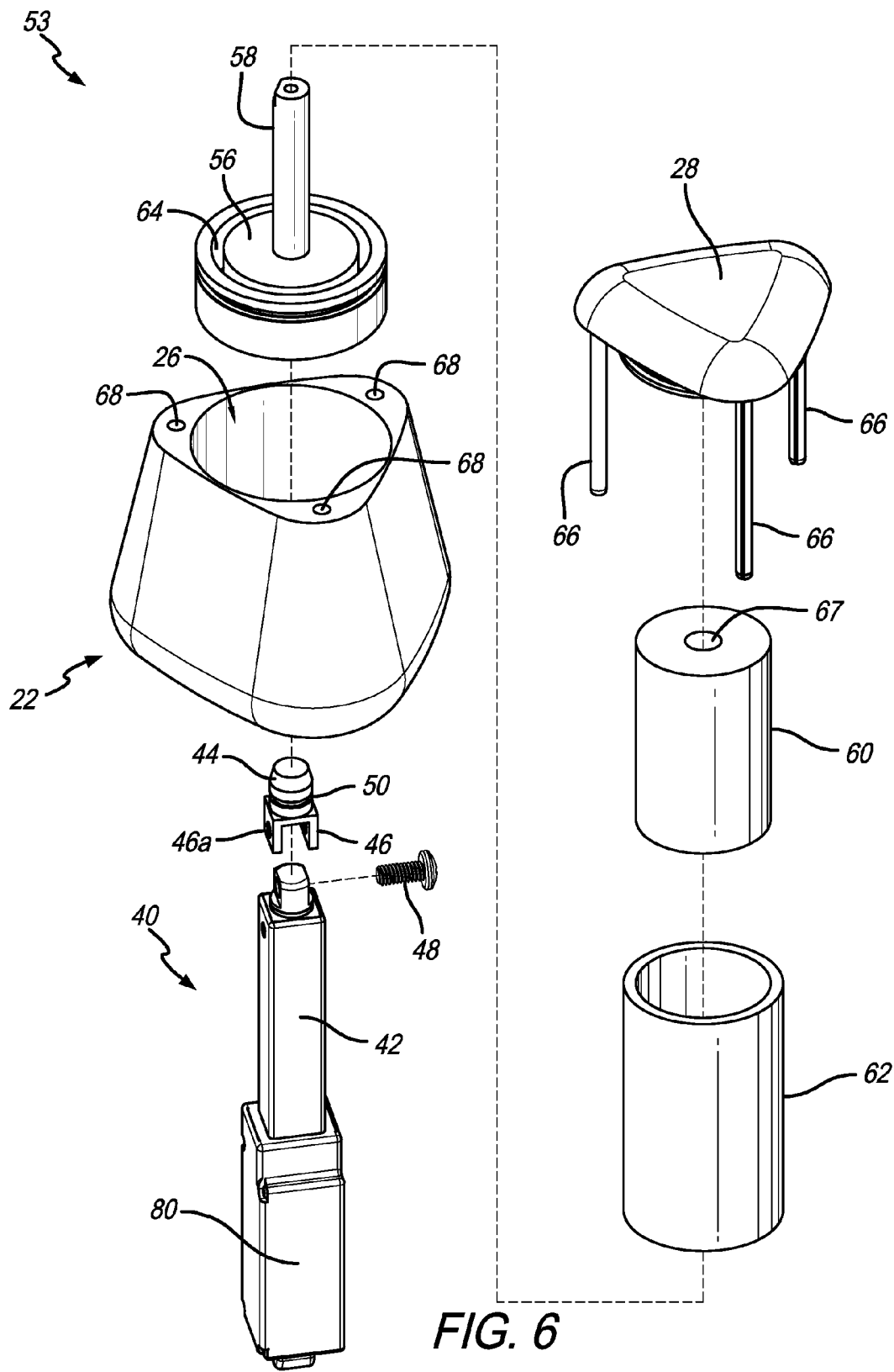
FIG. 6 is an exploded perspective view of a cartridge and actuator from the scent delivery assembly of FIG. 1.
Figure 7:
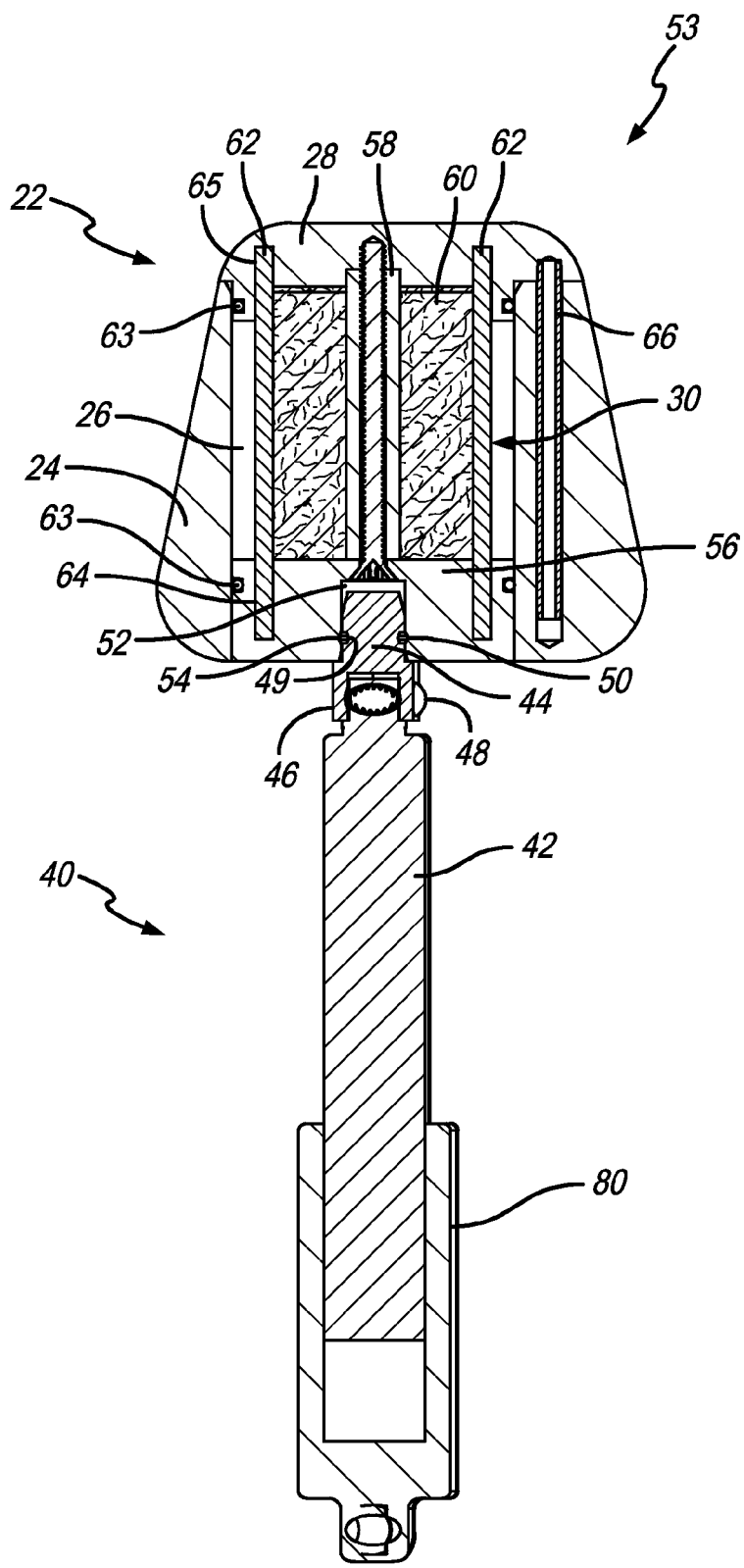
FIG. 7 is a cross-sectional view of a cartridge and actuator from the scent delivery assembly of FIG. 1.

FIGS. 6-7 show a cartridge 22 and actuator 40. In a preferred embodiment, the actuator 40 includes an arm 42 that is movable between a first position and a second position. The cartridge 22 is attached to a distal end of the arm 42. As shown in FIG. 4, the arms 42 extend through openings 34a in the divider member 34. Preferably, the cartridge 22 is removable from the arm 42 so that the cartridges 22 can be replaced during use. The connection between the cartridge 22 and the arm 42 can be any connection that allows the cartridge 22 to be replaced. In a preferred embodiment, the arm 42 includes a connection member 44 on the end thereof. The connection member 44 includes flanges 46 on the bottom thereof that include openings 46a therein that receive a screw 48 to connect the connection member 44 to the arm 42.

As shown in FIG. 7, the connection member 44 also includes a circumferential groove 49 defined in its outer diameter that receives a spring 50 therein. The connection member 44 is received in an opening 52 in the bottom of the cartridge 22. The cartridge 22 includes a groove 54 defined in the inner diameter that receives the spring 50. This provides a snap fit relationship so that the cartridge 22 can be removed from the distal end of the arm 42/connection member 44. It will be appreciated that other methods of connection between the arm and cartridge are within the scope of the present invention, e.g., the cartridge can be threaded onto the arm or a friction fit can be used. The actuator 40 and cartridge 22 are referred to herein together as a cartridge assembly 53. In a preferred embodiment, the force to install and remove the cartridge is sufficiently low to be done by hand (without tools), but enough force is required so that the cartridge is not disconnected during actuator operation and cartridge opening. However, this is not a limitation and in another embodiment, tools can be used.

In a preferred embodiment, the cartridge 22 includes a base member 56 in which opening 52 is defined. The base member 56 includes a shaft 58 extend therefrom that is connected at its distal end to the cover 28. The shaft 58 is the spool that receives the scent assembly 30. In a preferred embodiment, the scent assembly 30 includes a reservoir portion 60 and a diffusing portion 62. The diffusing portion 62 is tubular and is received in a circular groove 64 defined in the base member 56 (a similar circular groove 65 is defined in the cover 28). The reservoir portion 60 is received in the diffusing portion 62 and the shaft 58 is received in a central opening 67 in the reservoir portion 60. In a preferred embodiment, the cartridge includes O-rings 63 that are seated in grooves and that seal the movable cover 28 and base member 56 against the stationary housing portion 24. The O-rings 63 seal the cartridge every time it is closed to prevent scent contamination in the cabin and to prevent mixing of the scents when not in use.

It will be appreciated that the reservoir portion 60 is preferably made of a porous material that is impregnated with scented oil. In the open position, the diffusing portion 62 pulls the oil out of the reservoir portion 60 and evaporates it into the air as a result of the flow of air along the airflow path P1. Preferably, each of the cartridges 22 in the scent delivery assembly 10 includes a different scented oil in the reservoir portion 60. The scents can be diffused to instill different moods or simply different scents into the environment (e.g., the room 202 or volume within the aircraft 200; see FIG. 1). It will be appreciated that the scent assembly 30, including the reservoir portion 60 and the diffusing portion 62 can be any shape and is not limited to the cylindrical shape shown. For example, the scent assembly 30 can include a plurality of fins that extend in the same direction as the airflow. In another embodiment, the scent assembly 30 can include a plurality of openings therein. Generally, the scent assembly 30 includes the reservoir portion 60 that holds the scented oil and the diffusing portion 62. Any shape of the components is within the scope of the present invention provided the airflow flows over or through the diffusing portion and pulls the oil from the reservoir portion and moves the scent out in to the environment.

In a preferred embodiment, the cover 28 includes at least one and preferably three alignment rods 66 that extend therefrom and into alignment openings 68 that are defined in the housing portion 24. The movable portion of the cartridge 22 (e.g., the base member 56, scent assembly 30, cover 28, shaft 58 and alignment rods 66, etc.) are referred to together herein as the movable portion 70.

In a preferred embodiment, the scent delivery system 10 includes a plurality of positioning pegs 72 positioned adjacent the exterior surface of the cartridges. The positioning pegs 72 make it easier to position the cartridge 22 when replacing a used one with a new one and are provided for fixing or clamping the housing portion 24 within the airflow path portion 36.

Figure 5:
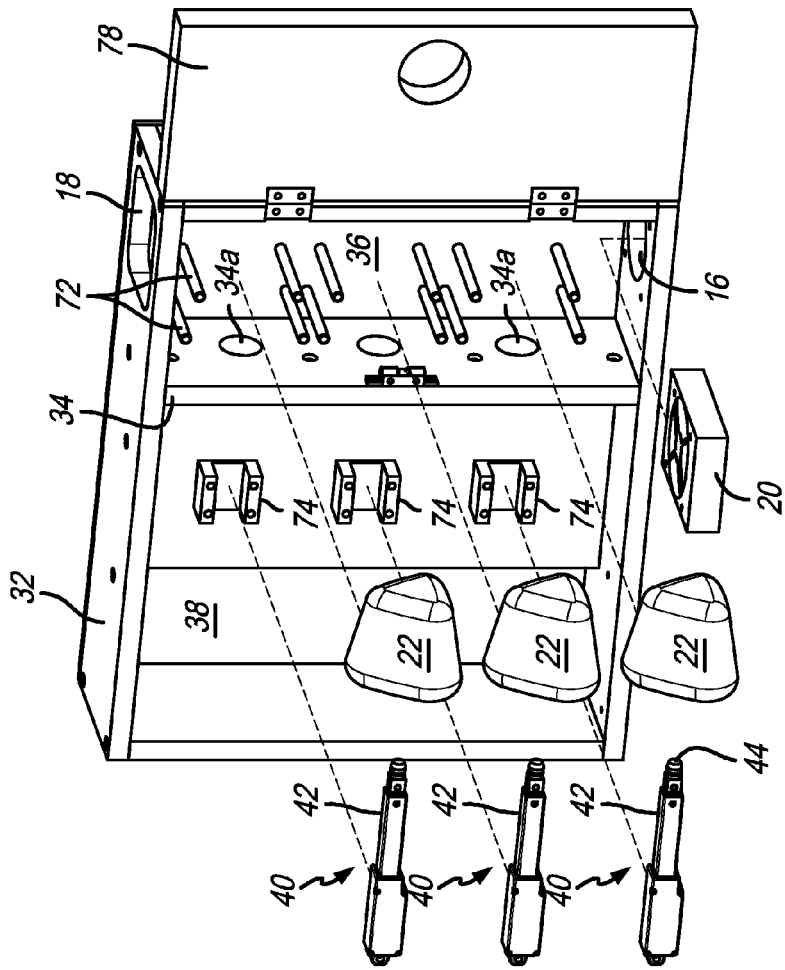
FIG. 5 is an exploded perspective view of the scent delivery assembly of FIG. 1.

As shown in FIGS. 3-5, in a preferred embodiment, the actuators 40 are attached via brackets 74 that are mounted on a mounting board 76 positioned in the non-airflow path portion 38. Another board 77 can be mounted on the opposite side of the actuators 40. In a preferred embodiment, the airflow path portion 38 is covered by a door 78 that is openable to replace the cartridges 22.

The actuators 40 can include any type of mechanism capable of extending the arm 42 in a linear manner. In a preferred embodiment the arm 42 is movable within a housing 80 that slidably receives the arm and houses the mechanism for extending and retracting the arm 42. The electronics for the actuator 40 are also preferably housed in the housing 80. The actuators 40 are in communication with and controlled by a controller 82 that is part of a printed circuit board or the like.

Figure 8:
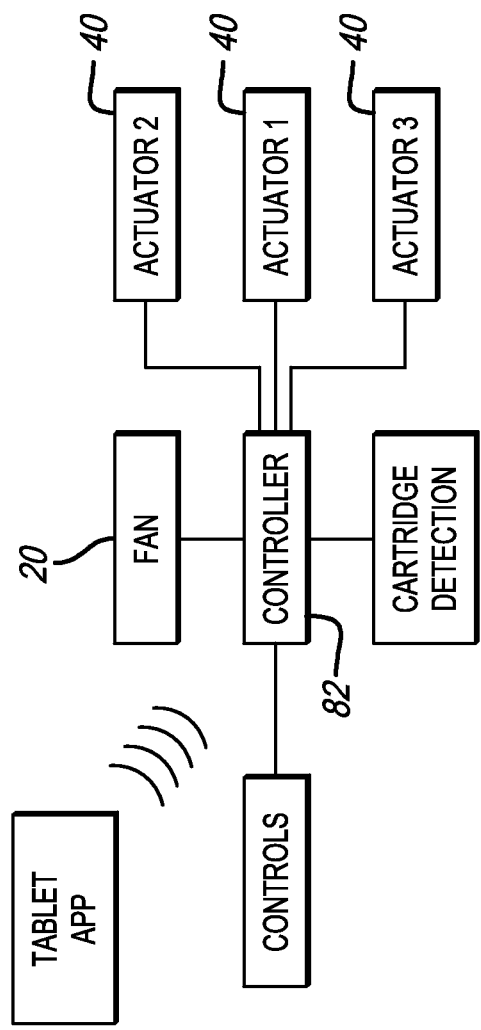
FIG. 8 is a schematic showing the communication between the controller, the cartridges and the fan.

FIG. 8 shows an exemplary embodiment of the communication between the controller 82 (which is preferably part of a PCB), the actuators 40, the fan 20, and the control panel. The controller and PCB are capable of communicating with the control panel (e.g., tablet, smart phone) wirelessly or on a device with buttons. It provides the actuators and fan proper input settings for selecting proper cartridge (from user selection) and proper settings (fan speed etc. . . . ) depending on room size, scent selected etc.

In a preferred embodiment, the controller 82 is in communication with the cartridges (e.g., through RFID or other wireless communication) so that the controller 82 can identify the particular scent associated with the cartridge and to monitor the cartridge (e.g., scent oil remaining, how long the cartridge has been in use, etc.). For example, the cartridge can include an RFID tag or other transmitter attached thereto and the controller can include a receiver to recognize the cartridge scent once installed. This will then populate the control pad or other human machine interface (e.g., tablet) so that it is apparent what scent is in the particular cartridge (e.g., energetic, calming, relaxing, etc.). Generally, it will be appreciated that the controller 82 can selectively move the covers 28 (and, therefore, the scent assemblies 30) between the open and closed positions.

In use, when a user wants to diffuse a scent into the environment, the user pushes a button or the like on the tablet or other control panel. The tablet communicates with the controller 82 of the scent delivery assembly 10, which, in turn, actuates the actuator 40 of the appropriate cartridge assembly 53. When the actuator 40 is actuated arm 42 moves from the first position to the second position and the movable portion 70 (which includes the cover 28) is moved from the closed position to the open position. Because the distal end of arm 42 is engaged with opening 52, as arm 42 moves to the second position it moves base member 56, which moves the scent assembly 30 and shaft 58 together with cover 28. The alignment rods 66 also move within alignment openings 68. The controller 82 also actuates fan 20, thereby pulling air through intake opening 16 and moving air along airflow path P1. As a result of air flowing over the exposed diffusing portion 62, oil is pulled from the reservoir portion 60, is expelled through outlet opening 18 and released into the environment.

In a preferred embodiment, as shown in FIG. 4, the cartridges 22 are positioned so that the scent assemblies 30 are generally out of the air flow path P1 when the covers 28 are in the closed position, and are extended into or are aligned with the airflow path P1 when the covers 28 are in the open position.

Figure 9:
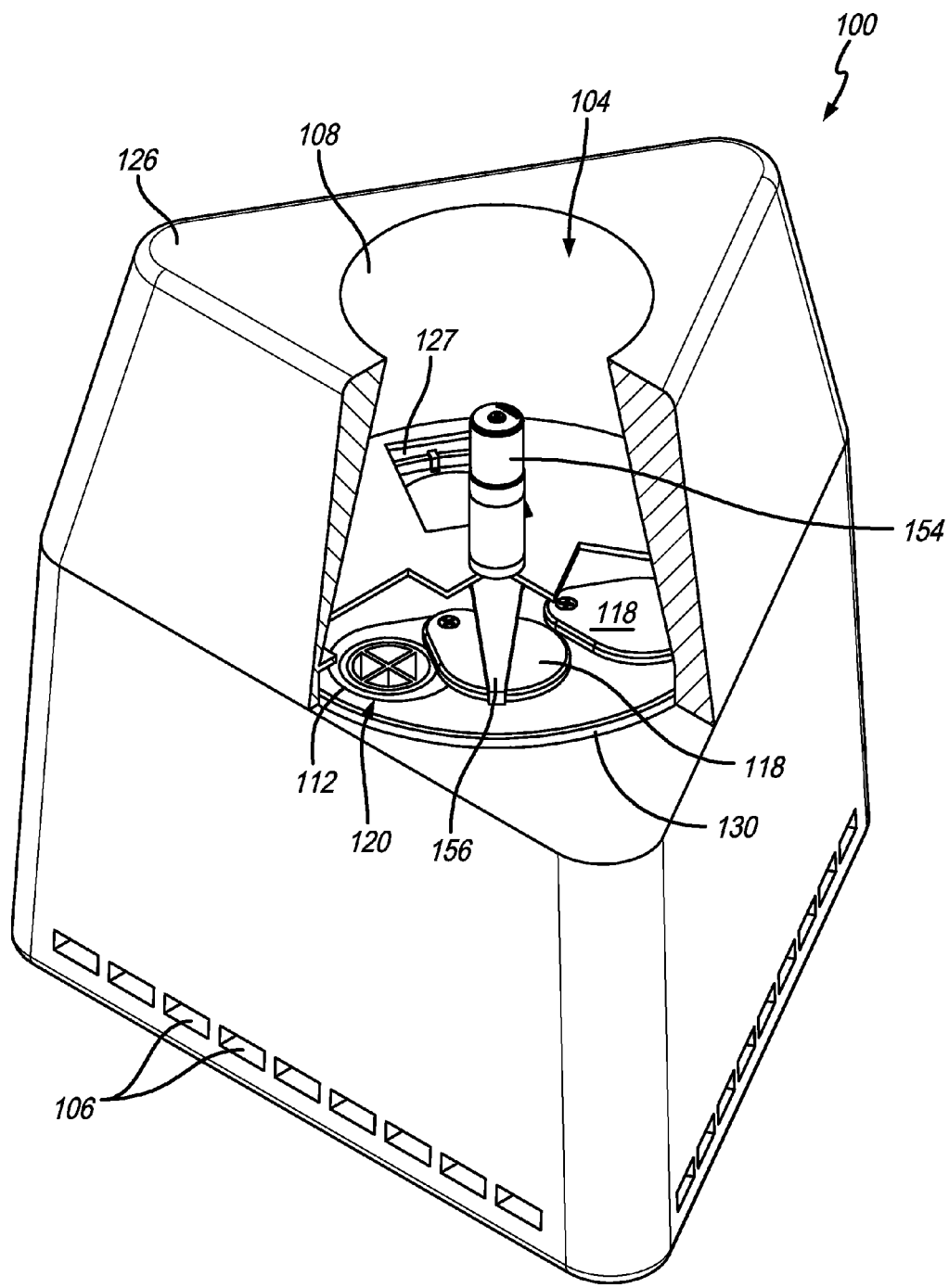
FIG. 9 is a perspective view of a scent delivery assembly in accordance with a preferred embodiment of the present invention with a portion of the upper housing portion cut away.
Figure 10:
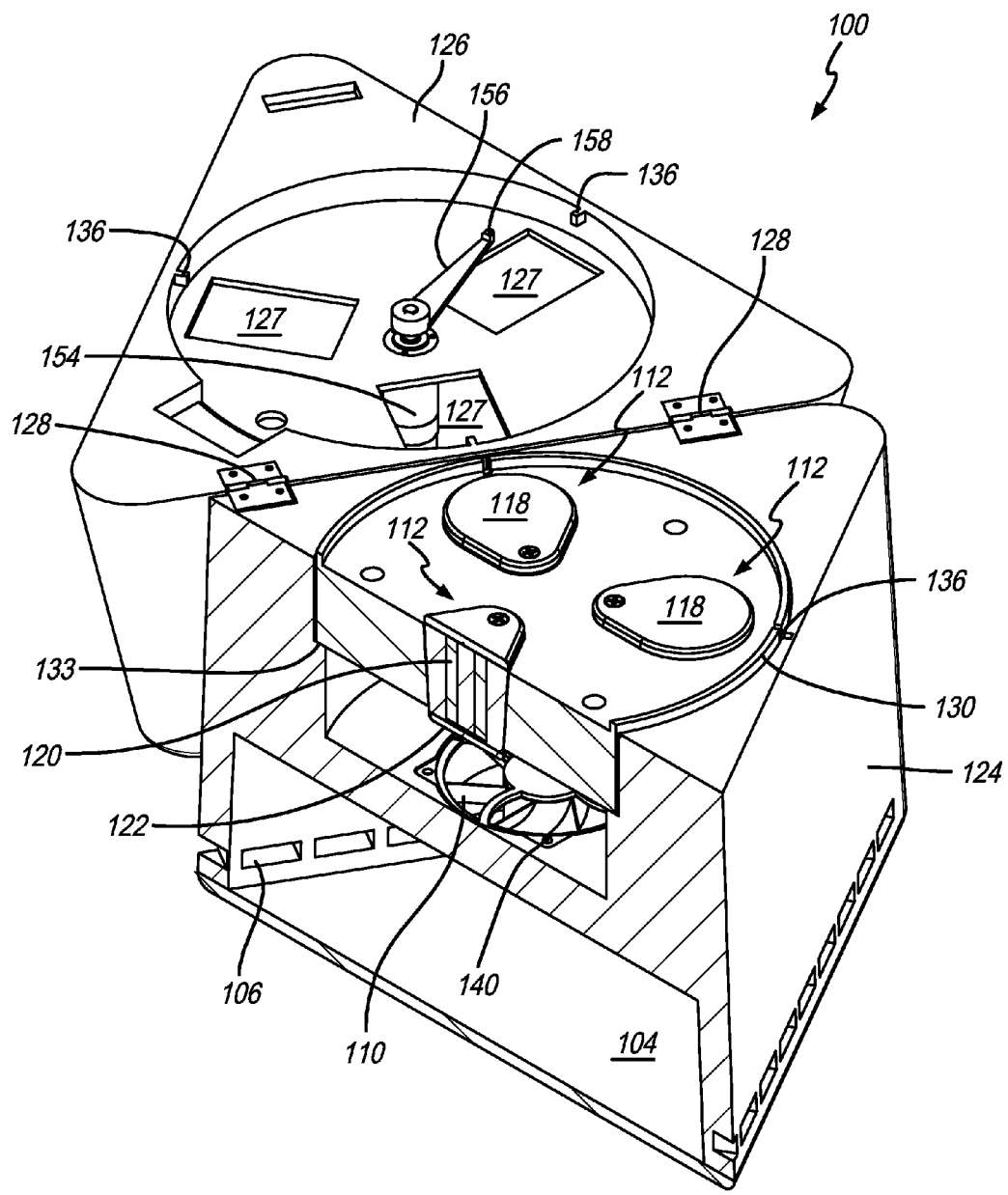
FIG. 10 is a perspective view of the scent delivery assembly of FIG. 9 with the upper housing portion hinged open and a portion of the lower housing portion in cross-section.
Figure 11:
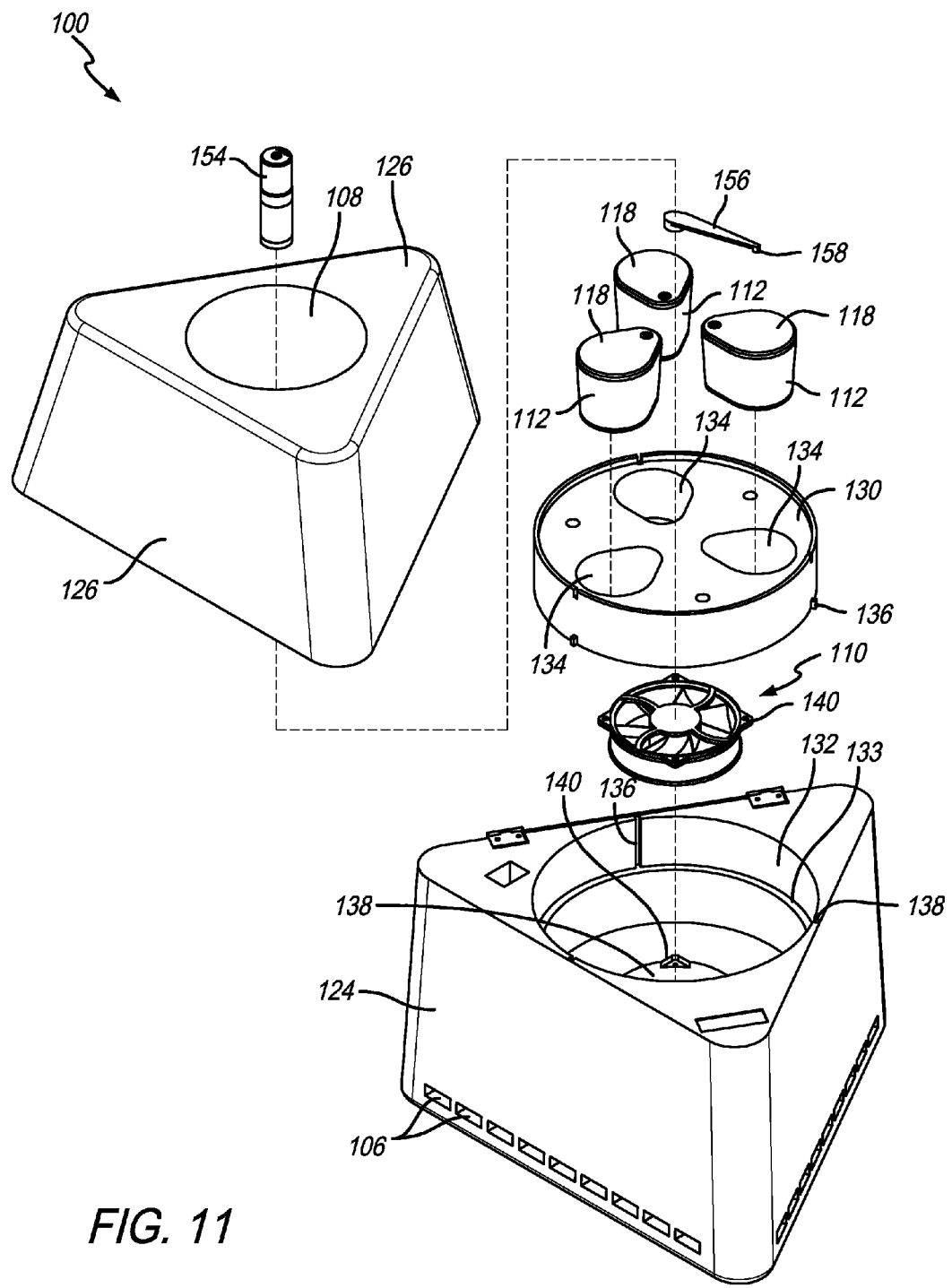
FIG. 11 is an exploded perspective view of the scent delivery assembly of FIG. 9.
Figure 12:
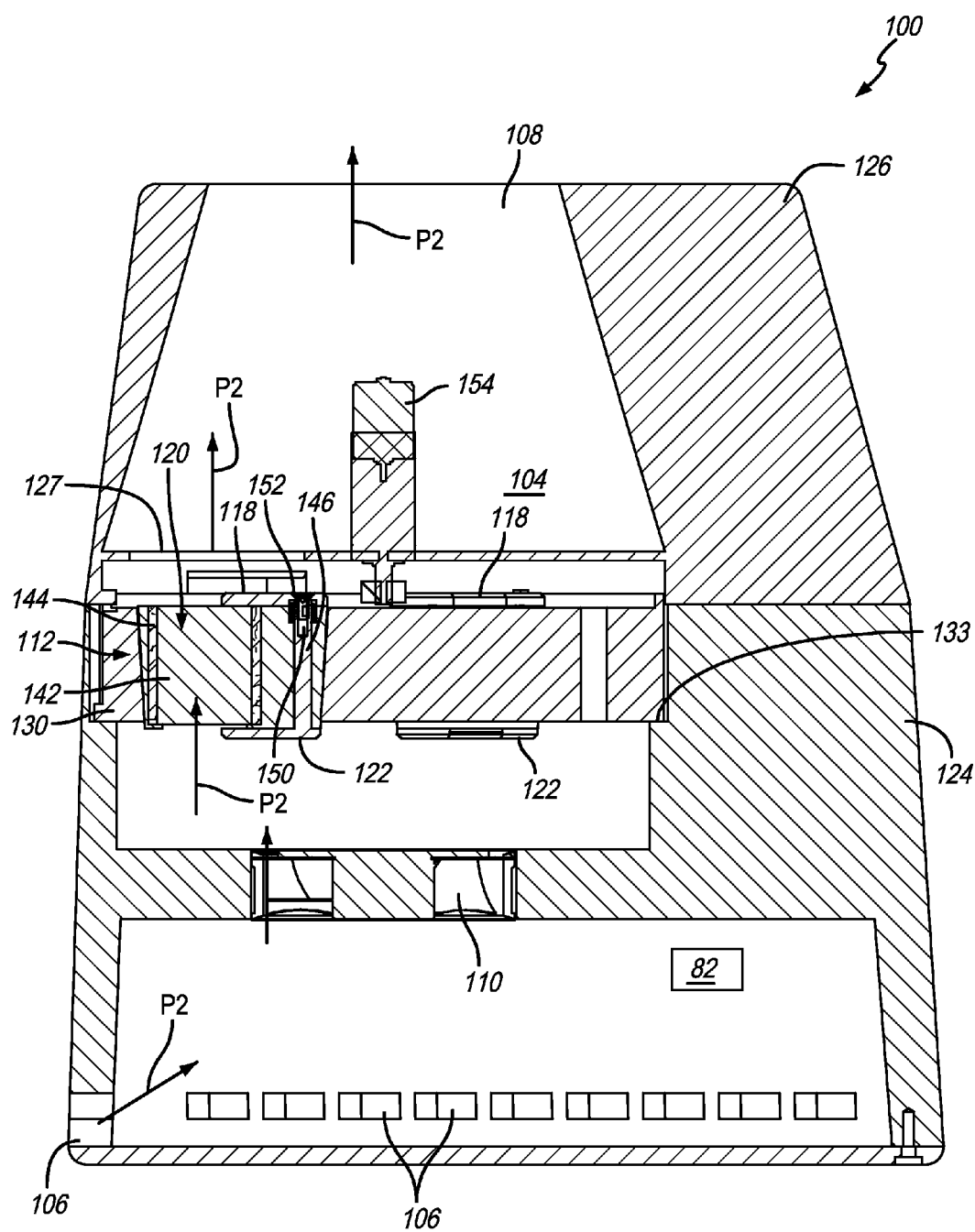
FIG. 12 is a cross-section of the scent delivery assembly of FIG. 9.
Figure 13:
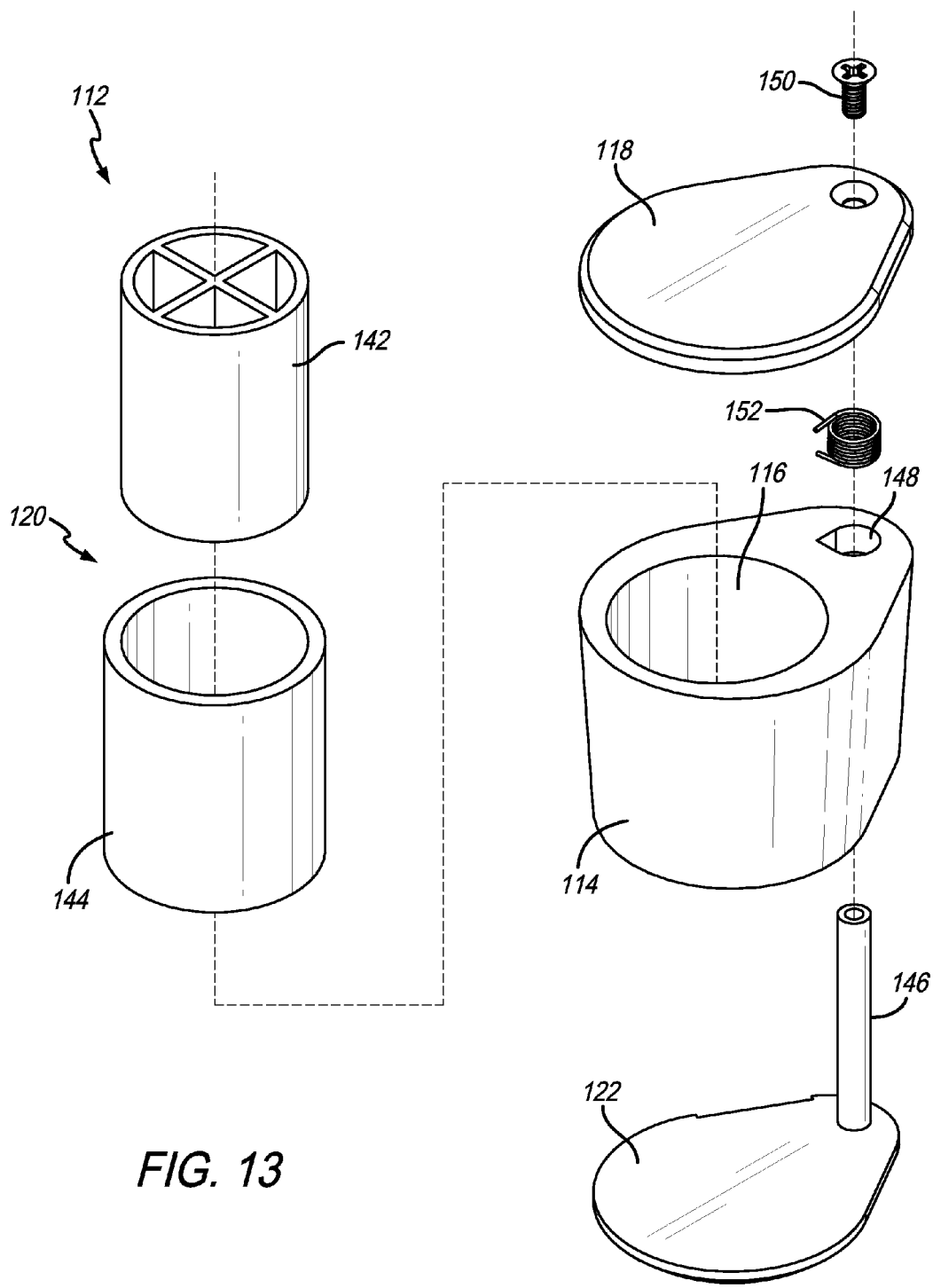
FIG. 13 is an exploded perspective view of a cartridge from the scent delivery assembly of FIG. 9.

With reference to FIGS. 9-13, scent delivery assembly 100 is shown and described. In a preferred embodiment, scent delivery assembly 100 includes a main body portion 102 that defines an interior 104 and includes at least one intake opening 106 and at least one outlet opening 108. As shown in FIG. 12, an airflow path P2 is defined between the intake opening 106 and the outlet opening 108. A fan 110 is positioned along the airflow path P2. At least one and preferably a plurality of cartridges 112 are positioned along the airflow path P2. As shown in FIG. 13, each cartridge 112 includes a housing portion 114 that defines a housing interior 116, a first cover 118 and a scent assembly 120 positioned in the housing interior 116. The first cover 118 is movable between a closed position and an open position. In a preferred embodiment, the cartridge 112 includes a second cover 122 that is movable together with the first cover 118 between the closed position and the open position. It will be appreciated that the scent assembly 120 is positioned between the first cover 118 and the second cover 122 when the first and second covers are in the closed position and is therefore not in flow communication with the airflow path P2 when the first and second covers are in the closed position. The scent assembly 120 is in flow communication with the airflow path P2 when the first and second covers 118 and 122 are in the open position. FIG. 9 shows one cartridge 112 with the first cover 118 in the open position and the other two cartridges 112 with their first covers 118 in the closed position.

As shown in FIGS. 9-12, in a preferred embodiment, the main body portion 102 includes a lower housing portion 124 and an upper housing portion 126 that cooperate to define the interior 104. The intake openings 106 are is defined in the lower housing portion 124 and the outlet opening 108 is defined in the upper housing portion 126. Preferably, the upper housing portion 126 is hingedly connected (see hinges 128) to the lower housing portion 126. However, in another embodiment, the upper housing portion 126 can be removable. As shown in FIG. 10, the upper housing portion 126 includes openings 127 therein that are generally aligned with the cartridges 112.

As shown in FIGS. 9-12, the scent delivery assembly 100 includes a removable tray portion 130 that is received in a tray portion recess 132 that is defined in the lower housing portion 124 and includes a ledge 133. The tray portion 130 includes a plurality of cartridge openings 134 that receive the cartridges 112. In a preferred embodiment, the housing portion 114 of the cartridges 112 is tapered and the cartridge openings 134 include a similar taper to hold the cartridges in place (the taper can be seen in FIG. 12), and allows them to be removed and replaced. In a preferred embodiment, the tray portion 130 and tray portion recess 132 include complementary male and female alignment members 136. In the drawings, the male alignment member is shown in the tray portion 130 and the female alignment members are shown defined in the lower housing portion 124 in the tray portion recess 132. However, this arrangement can be reversed. The upper housing portion 126 also includes alignment members 136 for aligning with the tray portion 130 The fan 110 is positioned in an opening 138 in the lower housing portion 124. Preferably, the fan 110 includes tabs 140 that mate with complementary tabs 140 on the lower housing portion to position and secure the fan 110.

FIG. 13 best shows a cartridge 112. As shown, the cartridge 112 includes the housing 114, with the interior 116, which is preferably a cylindrical opening, first and second covers 118 and 122 and the scent assembly 120. Preferably, the scent assembly 120 includes an inner diffusing portion 142 and an outer reservoir portion 144. The second cover 122 (the lower cover) has a pivot shaft 146 extending therefrom that extends through a pivot opening 148 defined in the housing portion 114. The pivot shaft 146 is connected to the first cover 118 by a threaded fastener 150. Preferably, a spring 152 (e.g., a torsion spring) is received on the pivot shaft 146 and into the pivot opening 148 and biases the first and second covers 118 and 122 toward the closed position. In another embodiment, the pivot shaft 146 can extend from the first cover 118. In another embodiment, the pivot shaft 146 can be removably connected (via a threaded fastener or the like) to both the first and the second cover. Similar to the first embodiment, the cartridges 112 reseal when closed to keep scent from diffusing therefrom.

As shown in FIGS. 9-11, in a preferred embodiment, the scent delivery assembly includes a motor 154 that is operable to move the first cover 118 (and, therefore, the second cover 122) between the open and closed positions. The motor 154 includes an arm 156 extending therefrom that includes a finger 158 on the distal end thereof. The motor 154 can move the arm in a rotational manner. In use, when the arm 156 rotates the finger 158 contacts the first cover 118 of a cartridge 112 and pivots the first cover 118 to the open position. To close the first cover 118, the arm 156 continues to rotate in the same direction, and, because of the curved shape of the first cover 118, once the arm 156 passes the first cover 118, the spring 152 biases the first cover 118 back to the closed position. Because the first cover 118 is connected to the second cover 122 via the shaft 146, the second cover 122 always pivots with the first cover 118. In another embodiment, the arm can rotate the opposite direction (of the opening direction) to allow the cover to close.

Similar to the embodiment described above, the scent delivery assembly 100 includes a controller 82 that controls the motor 154 and thereby the opening and closing of the first and second covers. The controller also controls the operation of the fan.

In use, when a user wants to diffuse a scent into the environment, the user pushes a button or the like on the tablet or other control panel. The tablet communicates with the controller 82 of the scent delivery assembly 10, which, in turn, actuates the motor 154. The motor 154 rotates the arm 156 such that the first cover 118 of the appropriate cartridge 112 is pivoted to the open position. Because shaft 146 is attached to second cover 122, the second cover 122 is also moved to the open position. This opens the scent assembly 120 to the airflow path P2. The controller 82 also actuates fan 110, thereby pulling air through intake openings 106 and moving air along airflow path P2. As a result of air flowing over the exposed diffusing portion 142, oil is pulled from the reservoir portion 144, is expelled through outlet opening 108 and released into the environment.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

The teachings of the disclosure provided herein can be applied to other systems, not necessarily the system described above. The elements and acts of the various embodiments described above can be combined to provide further embodiments. Any measurements described or used herein are merely exemplary and not a limitation on the present invention. Other measurements can be used. Further, any specific materials noted herein are only examples: alternative implementations may employ differing materials.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A scent delivery assembly comprising:
a main body portion that defines an interior and includes at least one intake opening and at least one outlet opening, wherein an airflow path is defined between the intake opening and the outlet opening,
a fan positioned along the airflow path, and
at least a first cartridge positioned along the airflow path, wherein the first cartridge includes a first cover that is movable between a closed position and an open position, wherein the first cartridge includes a scent assembly, wherein the scent assembly is not in flow communication with the airflow path when the first cover is in the closed position, and wherein the scent assembly is in flow communication with the airflow path when the first cover is in the open position,
a first motor that is operable to move the first cover between the open and closed positions,
wherein the main body portion includes a divider member positioned in the interior, wherein the divider divides the interior into an airflow path portion and a non-airflow path portion, wherein the first scent assembly is positioned in the airflow path portion when the first cover is in the open position and wherein the first motor is positioned in the non-airflow path portion.

2. The scent delivery assembly of claim 1 wherein the scent assembly includes a reservoir portion and a diffusing portion.

3. The scent delivery assembly of claim 2 further comprising a second cartridge positioned along the airflow path, wherein the second cartridge includes a first cover that is movable between a closed position and an open position, wherein the second cartridge includes a scent assembly, wherein the scent assembly is not in flow communication with the airflow path when the first cover is in the closed position, and wherein the scent assembly is in flow communication with the airflow path when the first cover is in the open position.

4. The scent delivery assembly of claim 3 further comprising a third cartridge positioned along the airflow path, wherein the third cartridge includes a first cover that is movable between a closed position and an open position, wherein the third cartridge includes a scent assembly, wherein the scent assembly is not in flow communication with the airflow path when the first cover is in the closed position, and wherein the scent assembly is in flow communication with the airflow path when the first cover is in the open position.

5. The scent delivery assembly of claim 4 further comprising a controller, wherein the controller is configured to selectively move the first, second and third covers between the open and closed positions.

6. The scent delivery assembly of claim 1 wherein the first motor includes a first arm that is movable between a first position and a second position, wherein the first cartridge is attached to a distal end of the first arm, wherein when the first arm is in the first position the first cover is in the closed position, and wherein when the first arm is in the second position the first cover is in the open position.

7. The scent delivery assembly of claim 1 wherein when the first cover is in the closed position the scent assembly is not aligned with the airflow path, and wherein when the first cover is in the open position the scent assembly is generally aligned with the airflow path.

8. The scent delivery system of claim 1 wherein the first motor includes an arm extending therefrom, wherein the arm is configured to move the first cover between the open and closed positions.

9. The scent delivery system of claim 1 wherein the cartridge is sealed when it is in the closed position.

10. The scent delivery system of claim 5 wherein the first, second and third cartridges each include a scent associated therewith and are configured to communicate the scent identification to the controller.

11. The scent delivery system of claim 10 wherein the controller is configured to communicate the scent identification to a control panel that includes a user interface.

12. A scent delivery assembly comprising:
a main body portion that defines an interior and includes at least one intake opening and at least one outlet opening, wherein an airflow path is defined between the intake opening and the outlet opening,
a fan positioned along the airflow path,
at least a first cartridge positioned along the airflow path, wherein the first cartridge includes a first cover that is movable between a closed position and an open position, wherein the first cartridge includes a scent assembly, wherein the scent assembly is not in flow communication with the airflow path when the first cover is in the closed position, and wherein the scent assembly is in flow communication with the airflow path when the first cover is in the open position, and
a first actuator that includes a first arm that is movable between a first position and a second position, wherein the first cartridge is attached to a distal end of the first arm, wherein when the first arm is in the first position the first cover is in the closed position, and wherein when the first arm is in the second position the first cover is in the open position,
wherein the main body portion includes a divider member positioned in the interior, wherein the divider divides the interior into an airflow path portion and a non-airflow path portion, wherein the first cartridge is positioned in the airflow path portion and the first actuator is positioned in the non-airflow path portion.

13. A scent delivery assembly comprising:
a main body portion that defines an interior and includes at least one intake opening and at least one outlet opening, wherein an airflow path is defined between the intake opening and the outlet opening,
a fan positioned along the airflow path, and
at least a first cartridge positioned along the airflow path, wherein the first cartridge includes a first cover that is movable between a closed position and an open position, wherein the first cartridge includes a scent assembly, wherein the scent assembly is not in flow communication with the airflow path when the first cover is in the closed position, and wherein the scent assembly is in flow communication with the airflow path when the first cover is in the open position, wherein the first cartridge includes a housing portion and the first cover, wherein the housing portion includes an attachment opening therein, and wherein the distal end of a first actuator arm is releasably received in the attachment opening.

14. A scent delivery assembly comprising:
a main body portion that defines an interior and includes at least one intake opening and at least one outlet opening, wherein an airflow path is defined between the intake opening and the outlet opening,
a fan positioned along the airflow path,
at least a first cartridge positioned along the airflow path, wherein the first cartridge includes a first cover that is movable between a closed position and an open position, wherein the first cartridge includes a scent assembly, wherein the scent assembly is not in flow communication with the airflow path when the first cover is in the closed position, and wherein the scent assembly is in flow communication with the airflow path when the first cover is in the open position, and
at least first and second positioning pegs positioned adjacent an exterior surface of the first cartridge.

15. A scent delivery assembly comprising:
a main body portion that defines an interior and includes at least one intake opening and at least one outlet opening, wherein an airflow path is defined between the intake opening and the outlet opening,
a fan positioned along the airflow path,
at least a first cartridge positioned along the airflow path, wherein the first cartridge includes a first cover that is movable between a closed position and an open position, wherein the first cartridge includes a scent assembly, wherein the scent assembly is not in flow communication with the airflow path when the first cover is in the closed position, and wherein the scent assembly is in flow communication with the airflow path when the first cover is in the open position, and
a motor that is operable to move the first cover between the open and closed positions, wherein the first cartridge includes a second cover that is movable via the motor together with the first cover between the closed position and the open position, and wherein the scent assembly is positioned in the airflow path between the first cover and the second cover.

16. A scent delivery assembly comprising:
a main body portion that defines an interior and includes at least one intake opening and at least one outlet opening, wherein an airflow path is defined between the intake opening and the outlet opening, wherein the main body portion includes a lower housing portion and an upper housing portion that cooperate to define the interior, wherein the intake opening is defined in the lower housing portion and the outlet opening is defined in the upper housing portion,
a fan positioned along the airflow path, and
at least a first cartridge positioned along the airflow path, wherein the first cartridge includes a first cover that is movable between a closed position and an open position, wherein the first cartridge includes a scent assembly, wherein the scent assembly is not in flow communication with the airflow path when the first cover is in the closed position, and wherein the scent assembly is in flow communication with the airflow path when the first cover is in the open position.

17. The scent delivery system of claim 16 further comprising a removable tray portion received in a tray portion recess defined in the lower housing portion, wherein the tray portion includes a first cartridge opening defined therethrough, wherein the first cartridge is removably received in the first cartridge opening.

18. The scent delivery system of claim 17 wherein the upper housing portion is pivotally connected to the lower housing portion.

* * * * *